US012784567B2

(12) United States Patent
Dechant et al.

(10) Patent No.: US 12,784,567 B2
(45) Date of Patent: Nov. 3, 2026

(54) WEARABLE DEVICE FOR PREDICTING AND PREVENTING PATIENT FALLS

(71) Applicant: Christiana Care Health System, Inc., Wilmington, DE (US)

(72) Inventors: Laura Dechant, Aston, PA (US); Jennifer Irene Holding, Newark, DE (US); Kelsey Ann Kosinski, Wilmington, DE (US); Amanda Elyse Latina, Wilmington, DE (US)

(73) Assignee: CHRISTIANA CARE HEALTH SYSTEM, INC., Wilmington, DE (US)

( * ) Notice: Subject to any disclaimer, the term of this patent is extended or adjusted under 35 U.S.C. 154(b) by 50 days.

(21) Appl. No.: 18/804,643

(22) Filed: Aug. 14, 2024

(65) Prior Publication Data

US 2025/0061793 A1 Feb. 20, 2025

Related U.S. Application Data

(60) Provisional application No. 63/532,935, filed on Aug. 16, 2023.

(51) Int. Cl.
*G08B 21/04* (2006.01)
*A61B 5/11* (2006.01)

(52) U.S. Cl.
CPC ....... *G08B 21/0446* (2013.01); *G08B 21/043* (2013.01); *A61B 5/1117* (2013.01)

(58) Field of Classification Search
CPC .. G08B 21/0446; G08B 21/043; A61B 5/1117
USPC ...................................................... 340/573.1
See application file for complete search history.

(56) References Cited

U.S. PATENT DOCUMENTS

| | | | | |
|---|---|---|---|---|
| 9,149,222 | B1 * | 10/2015 | Zets | A61B 5/4023 |
| 9,311,789 | B1 * | 4/2016 | Gwin | G08C 19/00 |
| 10,055,948 | B2 * | 8/2018 | Kim | A61B 5/1114 |
| 10,194,837 | B2 * | 2/2019 | Kanchan | A61B 5/6806 |
| 10,198,928 | B1 * | 2/2019 | Ross | A61B 5/746 |
| 10,318,708 | B2 * | 6/2019 | Balakrishnan | G16H 15/00 |
| 10,575,760 | B2 * | 3/2020 | Houmanfar | A61B 5/05 |
| 11,967,217 | B1 * | 4/2024 | Andrews | G08B 29/186 |
| 2008/0129518 | A1 * | 6/2008 | Carlton-Foss | G08B 25/009 379/45 |
| 2009/0137933 | A1 * | 5/2009 | Lieberman | A61B 5/1117 600/595 |
| 2011/0251520 | A1 * | 10/2011 | Shieh | G16H 50/30 600/587 |

(Continued)

*Primary Examiner* — Zhen Y Wu
(74) *Attorney, Agent, or Firm* — FisherBroyles LLP

(57) ABSTRACT

Each of a set of wearable sensor bands includes a sensor for collecting movement data. The data is analyzed, from one band or both bands in combination, to determine whether ambulation of the wearer is imminent. The data may be analyzed by a data processor in a band or in a remote computing device. When the data indicates that ambulation is imminent, a control signal is used to provide an intervention to prevent the ambulation, and thereby to avoid a possible fall. The control signal may be transmitted to a band to drive an on-band feedback device to provide an alert to the wearer, or may be transmitted to a feedback device separate from the bands, e.g., a sign or speaker mounted in a hospital, to provide an alert to the wearer or the wearer's caregiver, or may be transmitted to a computing or other device monitored by a caregiver.

26 Claims, 3 Drawing Sheets

(56) References Cited

U.S. PATENT DOCUMENTS

| | | | | |
|---|---|---|---|---|
| 2014/0085082 | A1* | 3/2014 | Lyon | A61B 5/0004 340/539.12 |
| 2014/0111414 | A1* | 4/2014 | Hayner | G06F 3/016 345/156 |
| 2014/0145848 | A1* | 5/2014 | Amir | G08B 21/0492 702/150 |
| 2014/0276242 | A1* | 9/2014 | Chen | A61B 5/1116 600/595 |
| 2015/0087995 | A1* | 3/2015 | Murai | A61B 5/684 600/595 |
| 2015/0112162 | A1* | 4/2015 | Wilmink | G16H 50/30 600/306 |
| 2015/0366504 | A1* | 12/2015 | Connor | A61B 5/6804 600/301 |
| 2016/0203692 | A1* | 7/2016 | Ten Kate | G08B 21/0446 340/573.1 |
| 2016/0256082 | A1* | 9/2016 | Ely | A61B 5/7282 |
| 2016/0262685 | A1* | 9/2016 | Wagner | A61B 5/1128 |
| 2017/0094450 | A1* | 3/2017 | Tu | A61B 5/681 |
| 2017/0352240 | A1* | 12/2017 | Carlton-Foss | A61B 5/1116 |
| 2018/0000385 | A1* | 1/2018 | Heaton | G08B 25/016 |
| 2019/0228632 | A1* | 7/2019 | Hassey | G08B 21/182 |
| 2020/0294674 | A1* | 9/2020 | Emmons | A61B 5/0205 |
| 2021/0027599 | A1* | 1/2021 | Chan | G08B 7/06 |
| 2021/0209921 | A1* | 7/2021 | Lin | A61B 5/6828 |
| 2021/0236066 | A1* | 8/2021 | Wright | A61B 5/024 |
| 2023/0298726 | A1* | 9/2023 | Kanchan | G16H 20/30 706/12 |
| 2023/0341518 | A1* | 10/2023 | Rajab | A61B 5/1118 |
| 2023/0364469 | A1* | 11/2023 | Discenzo | A61B 5/112 |
| 2024/0024687 | A1* | 1/2024 | Schaer | A61N 1/36542 |

* cited by examiner

WEARABLE DEVICE FOR PREDICTING AND PREVENTING PATIENT FALLS

CROSS-REFERENCE TO RELATED APPLICATION

This application claims the benefit of priority under 35 U.S.C. § 119(e) of U.S. Provisional Patent Application No. 63/532,935, filed Aug. 16, 2023, the entire disclosure of which is hereby incorporated herein by reference.

FIELD OF THE INVENTION

The present invention relates generally to prevention of falls that may result in injuries to patients and others, and more particularly to a wearable monitoring device operable to predict and prevent patient falls and to avoid fall-related injuries.

DISCUSSION OF RELATED ART

Elderly persons, patients recuperating post-surgery, and persons with various afflictions have a heightened risk of falling and sustaining injuries as a result of a fall. Hospitals, nursing homes, and other entities that care for patients are particularly interested in reducing falls, and particularly in avoiding falls while a person is in their care.

The risk of falling increases with age, but it can be affected by a number of factors, including: age (the risk of falling increases significantly after the age of 65), health conditions (certain health conditions, such as arthritis, diabetes, and heart disease, can increase the risk of falling), medications (some medications, such as sedatives and antidepressants, can increase the risk of falling), vision problems (vision problems can make it difficult to see obstacles and can increase the risk of falling), foot problems (foot problems such as pain or poor circulation can make it difficult to walk and can increase the risk of falling) and environmental hazards (hazards such as uneven surfaces, loose rugs, and poor lighting can increase the risk of falling).

Taking steps to reduce fall risk can help keep a person safe and independent. Additionally, the cost of falls can be significant both to the individual who falls and to society as a whole. Falls can lead to a variety of injuries, including fractures, head injuries, and spinal cord injuries. These injuries can require hospitalization, surgery, and rehabilitation, which can be very costly.

In addition, falls can lead to lost productivity. As people who are injured may be unable to work, the total cost of falls in the United States is estimated to be $50 billion per year. This cost is borne by a variety of sources, including Medicare, Medicaid, private insurance, and out-of-pocket payments.

Falls are the leading cause of injury-related deaths in people over the age of 65, and they are a major cause of disability.

Currently, the monitoring of a patient can be done in various ways, ranging from manual observation to bed alarm systems. Manual observation can be resource intensive, requiring the maintaining of a constant visual of the patient by nurses/providers sitting next to the patient's bed or through video observation. Bed alarms reduce the necessary clinical resources needed for manual observation but are not predictive. The bed alarms are generally weight-controlled and configured to sound only if there is a negative change in weight. However, this change in weight occurs only after the patient has already left the bed, and thus is issued too late for a nurse/provider to provide intervention before a possible fall.

What is needed is a device that does not require manual observation, and that provides an alert to an assistive caregiver and/or an intervention in the event of predicted ambulation, prior to a patient's leaving a bed, so that an intervention can be provided before a possible fall.

SUMMARY

The present invention provides a device that does not require manual observation, and that provides an alert to an assistive caregiver and/or an intervention in the event of predicted ambulation, prior to a patient's leaving a bed, so that an intervention can be provided before a possible fall. More particularly, the present invention provides a set of sensor bands that are configured to be wearable on the limbs or other portions of a living being.

Each sensor band includes at least one sensor operatively configured to collect sensor data associated with band movement, such that movement of the body of the living being can be predicted based on the sensor data. The sensor data is analyzed to determine whether ambulation of the living being is imminent. The sensor data from the bands, either alone or in combination, may be analyzed by a data processor in at least one of the bands, or in a remote computing device. When the processing of the sensor data is determined to indicate that ambulation of the living being is imminent, a control signal is used to provide an intervention to prevent the ambulation, and thereby to avoid a possible fall. The control signal may be transmitted to a sensor band to drive a feedback device of the sensor band to provide an alert to the living being, or may be transmitted to a feedback device separate from the sensor bands, e.g., mounted on a wall in a hospital, to provide an alert to the living being of the living being's caregiver, or may be transmitted to a computing or other device monitored by a caregiver, e.g., at a nurse's station.

BRIEF DESCRIPTION OF THE FIGURES

An understanding of the following description will be facilitated by reference to the attached drawings, in which.

DETAILED DESCRIPTION

Figure 1:
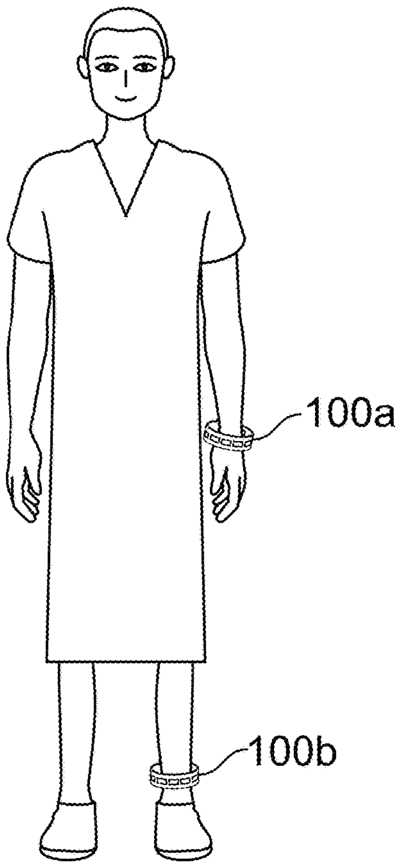
FIG. 1 shows a front view of an exemplary patient wearing an exemplary set of sensor bands around the wrist and ankle in accordance with an exemplary embodiment of the present invention.
Figure 2:
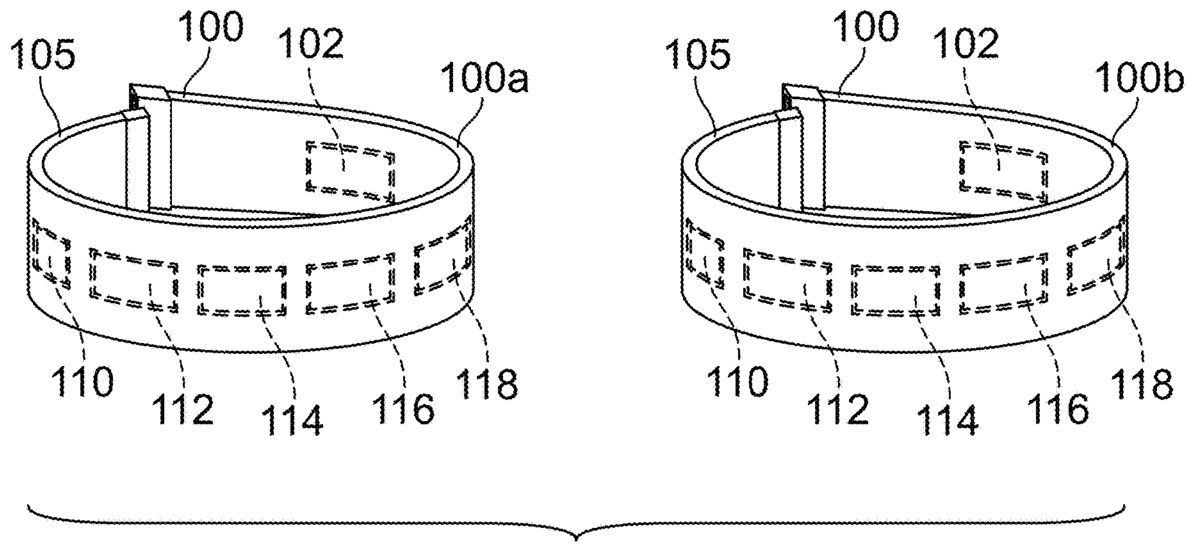
FIG. 2 is a perspective view of the set of sensor bands of FIG. 1, in accordance with an exemplary embodiment of the present invention.

The present invention provides a wearable device in the nature of a set 100 of sensor bands 100*a*, 100*b*, as shown in FIGS. 1 and 2. The two sensor bands 100*a*, 100*b*, are configured and/or intended to be worn on two different parts of the body.

By way of example, the set of sensor bands 100 may be worn by an inpatient during a hospital stay. In a typical arrangement, a patient may wear one sensor band 100*a* of the set 100 around the wrist and the other sensor band 100*b* of the set 100 another around the ankle, as shown in FIG. 1. Each sensor band 100*a*, 100*b* includes a mounting body 105, such as an elastic band or strap with a clasp/closure/buckle.

Figure 3:
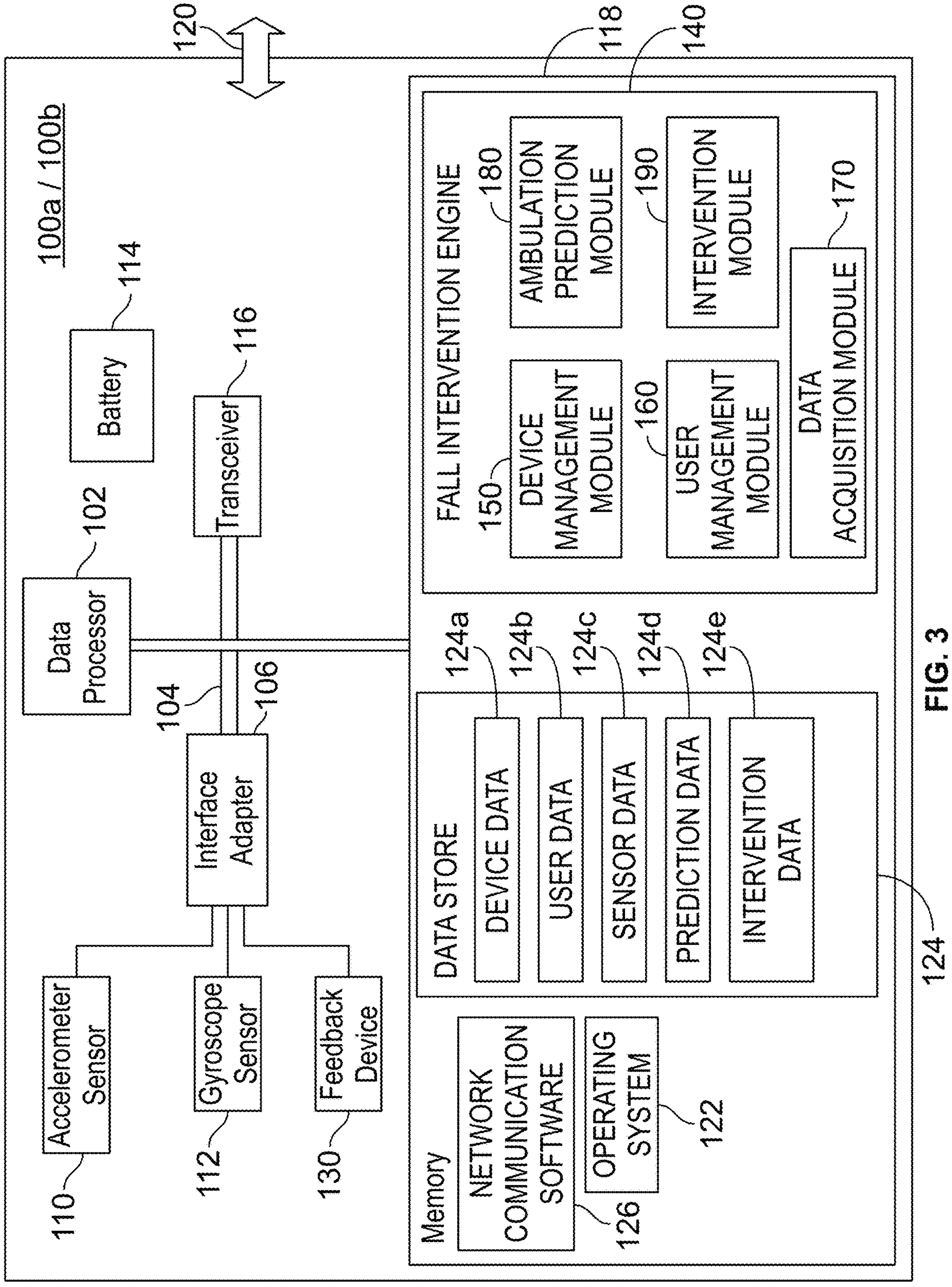
FIG. 3 is a schematic diagram showing components of an exemplary sensor band of FIG. 2, in accordance with an exemplary embodiment of the present invention.

Further, as shown in FIGS. 2 and 3, each sensor band 100*a*, 100*b* includes at least one sensor operable to collect data associated with movements of the sensor/band such as accelerations of the body and the movements/rotations, e.g., about a spatial axis. By way of example, such as an accelerometer 110 and gyroscope 112, e.g., of a type generally similar to those commonly used in conventional smartphones. Accordingly, movement data gathered by the sensor(s) of the sensor band is representative of movement of the corresponding body part on which the sensor band 100*a*, 100*b* is worn.

Additionally, each sensor band 100*a*, 100*b* may include a data communication transmitter and/or transceiver (collectively, "transceiver") 114, a data processor 102, a memory 118 and a battery 116 operatively connected to the sensor(s) 110, 112, transceiver 114, data processor 102, and memory 116, as will be appreciated from FIGS. 2 and 3.

Each sensor band's sensors collect sensor/body movement data that is used to determine if the motion is predictive of a patient attempting to get out of bed, leave a chair, etc. By way of example, x/y/z coordinate data (comparing the respective positions and/or orientations in space across the two bands worn by a user in embodiments in which each band has a global positioning system (GPS) or other sensor capable of providing such data), acceleration data, spatial orientation data, etc. may be gathered by the sensors 110, 122 of the sensor bands 100*a*, 100*b*. In certain embodiments, this may involve analyzing each band's sensor data in relation to the other band's sensor data, and/or analyzing the data from both sensor bands together.

The sensor data is analyzed to determine whether the data indicates that it is likely that the person/patient is preparing/attempting to leave a bed, chair, etc., and thus is likely to soon being to stand/walk, etc. When it is determined that the movement data captured is deemed to correspond to an attempt to leave the bed, chair, etc., a control signal is provided to deliver an intervention to stop the patient from exiting the bed, etc., or to signal the patient to stop exiting of the bed, await assistance, etc., as discussed in greater detail below.

In certain embodiments, each sensor band 100*a*, 100*b* may further include a feedback device 130 for providing an intervention in the nature of an alert provided to the wearer of the sensor band. By way of example, the feedback device 130 may be a buzzer or vibratory motor providing palpable/haptic feedback, a lamp providing visible feedback, or a speaker or other device providing audible feedback (such as an alarm tone or audible spoken word message), to the wearer of the sensor band. In such instances, the feedback device 130 may be responsive to a control signal causing the buzzer or vibratory motor to be driven to provide palpable feedback, or causing speaker or other device to provide the audible feedback. In this manner, the patient may be prevented from unassisted ambulation, and a resulting fall can be avoided.

In other embodiments, the feedback device may be provided as a device in the patient's hospital room, e.g., a speaker device 400*b*. In this manner, unassisted ambulation of the patient, and a resulting fall, can be avoided. In this manner, the patient may be prevented from unassisted ambulation, and a resulting fall can be avoided.

FIG. 3 is a schematic diagram showing components of an exemplary sensor band 100*a*, 100*b* of FIG. 2, in accordance with an exemplary embodiment of the present invention. In other embodiments a simpler sensor band may be used, as will be appreciated by those skilled in the art. However, in this example, the exemplary sensor band 100*a*/100*b* includes conventional computing hardware storing and executing conventional software enabling operation of a general-purpose computing system, such as operating system software 222 and network communications software 226. Additionally, this exemplary sensor band 100*a*/100*b* stores and executes additional computer software for carrying out at least one method in accordance with the present invention. By way of example, the communications software 226 may include conventional data communications software, and the operating system software 222 may include IOS, Android, Windows, Linux and/or other software.

Accordingly, the exemplary sensor band 100*a*/100*b* of FIG. 3 includes a data processor, such as a microprocessor (CPU) or other general-purpose processor 202 and a bus 204 employed to connect and enable communication between the processor 202 and the components of the sensor band 100*a*/100*b* in accordance with known techniques. The exemplary sensor band 100*a*/100*b* includes an interface adapter 206, which connects the processor 202 via the bus 204 to one or more interface devices, such as accelerometer sensor 110, gyroscope sensor 112 and feedback device 130. In certain embodiments, the sensor band 100*a*/100*b* may not include all of these interface devices. The bus 204 also connects the processor 202 to memory 118, which can include solid state or other memory. A battery 116 is operatively connected to the sensor(s) 110, 112, transceiver 114, data processor 102, memory 116 and feedback device 130, e.g., via the bus 104 or a separate bus.

The sensor band 100*a*/100*b* may communicate with other devices, computers or networks of computers, for example via a communications channel 220, via the transceiver (which may include a network card and/or modem) 114. The sensor band 100*a*/100*b* may be associated with such other computers in a local area network (LAN) or a wide area network (WAN), and may operate as a server in a client/server arrangement with another computer, etc. Such configurations, as well as the appropriate communications hardware and software, are known in the art.

The sensor band 100*a*/100*b* includes computer-readable, processor-executable instructions stored in the memory 118 for carrying out the methods described herein. Further, the memory 118 stores certain data, e.g. in one or more databases or other data stores 124 shown logically in FIG. 3 for illustrative purposes, without regard to any particular embodiment in one or more hardware or software components.

Further, as will be noted from FIG. 3, the sensor band 100*a*/100*b* includes, in accordance with the present invention, a Fall Intervention Engine (FIE) 140, shown schematically as stored in the memory 118, which includes a number of modules providing functionality in accordance with the present invention, as discussed in greater detail below. These modules may be implemented primarily by software including microprocessor-executable instructions stored in the memory 118 of the sensor band 100*a*/100*b*. Optionally, other software may be stored in the memory 118 and and/or other data may be stored in the data store 124 and/or memory 118.

As referenced above, the sensor band 100*a*/100*b* processes the data received from the sensor(s) 110, 112 to predict walking movement that can lead to falls, and in some cases, to initiate an intervention, either indirectly by sending a control signal that prompts a caregiver to provide the intervention, or directly by transmitting a control signal to a feedback device of the sensor band 100*a*/110*b* providing an alert to the wearer of the sensor band 100*a*/100*b* that prompts the wearer to take action to avoid a fall, as described in greater detail above and below.

Accordingly, as shown in FIG. 3, the exemplary FIE 140 of the exemplary sensor band 100*a*/100*b* includes a Device Management Module (DMM) 150. The DMM 150 is responsible for tracking of data relating to battery life, a unique sensor band identifier and/or other aspects of operation of the sensor band 100*a*/100*b*, to create, store and/or retrieve/send a sensor band-specific profile for each sensor band 100*a*/100*b*. Accordingly, the DMM 150 may retrieve data from and/or store data in the Data Store 224 as Device Data 224*a*. This allows each sensor band 100*a*/100*b* to be tracked individually with respect to battery life, operation, etc. in an identifiable manner, e.g., centrally at a nurse's station.

Further, as shown in FIG. 3, the exemplary FIE 140 of the exemplary sensor band 100*a*/100*b* includes a User Management Module (UMM) 150. The UMM 160 is responsible for tracking of data relating to a wearer/user of the sensor band, such as a unique patient/person identifier and/or other aspects of wearer's profile, to create, store and/or retrieve/send a wearer/user-specific profile for the sensor band 100*a*/100*b*. Accordingly, the UMM 160 may retrieve data from and/or store data in the Data Store 224 as User Data 224*b*. This allows each user/wearer and associated data to be tracked individually in an identifiable manner, e.g., centrally at a nurse's station.

Further, as shown in FIG. 3, the exemplary FIE 140 also includes a Data Acquisition Module (DAM) 170. The DAM 170 is responsible for receiving sensor data from the sensor(s) 110/112 and storing such data in the Data Store 224 as Sensor Data 224*c*. The Sensor Data 224*c* may be stored in a manner to associate it with a particular patient/person to which it pertains, as that person is identified in the User Data 224*b*. This allows the received Sensor Data 224*c* for a particular person to be processed to perform an ambulation prediction for that person using the applicable Sensor Data 224*c*.

Further still, as shown in FIG. 3, the exemplary FIE 140 also includes an Ambulation Prediction Module (APM) 180. The APM 180 is responsible for processing sensor data from the sensor(s) 110/112, etc. (which may involve use of the general-purpose processor 202 and/or retrieving of appropriate sensor Data 224*c* from the Data Store 224). More particularly, APM 180 is responsible for processing the sensor data to predict whether walking movement is imminent as a function of the sensor data. For example, the x/y/z coordinates of each band are compared and the relative location of the bands will show that walking movement is imminent, if one band is significantly higher than and in significant vertical alignment of the other band indicating the person is attempting to sit/stand up.

Further, acceleration and movement data received from the accelerometer and gyroscope sensors 110, 112 may be processed to determine whether/when the person is beginning to move in a way suggesting that ambulation is likely to be imminent. Notably, data from movements can be used that are prior to walking/ambulation movements.

By way of example, such processing of sensor data to determine whether walking movement is imminent (including occurring) may involve comparing sensor data from one band 100*a* to sensor data from another band 100*b*, and/or combining data from both bands to reach a conclusion as to whether ambulation is imminent.

The sensor data may be continuously/repeatedly monitored and assessed by the APM 180 over time.

Results of the ambulation prediction may be stored as Prediction Data 124*d* in the Data Store.

In this example shown in FIG. 3, the FIE 140 further includes an Intervention Module (IM) 190. The IM 190 is responsible for transmitting a control signal, e.g., using Intervention Data 124*e* stored in the Data Store 124 in association with the particular person and/or set of sensors.

In certain embodiments, the IM 190 is configured to initiate an intervention by sending a control signal to a feedback device 130 of the sensor band 100*a*/100*b*, to cause the feedback device 170 to provide haptic or audible feedback directly to the wearer of the sensor band, so that the person can be alerted and prompted to take corrective action to avoid a fall, such as not leaving a bed. For example, the IM 190 may send a control signal to cause playing of an audible message not to stand/walk without assistance.

Figure 4:
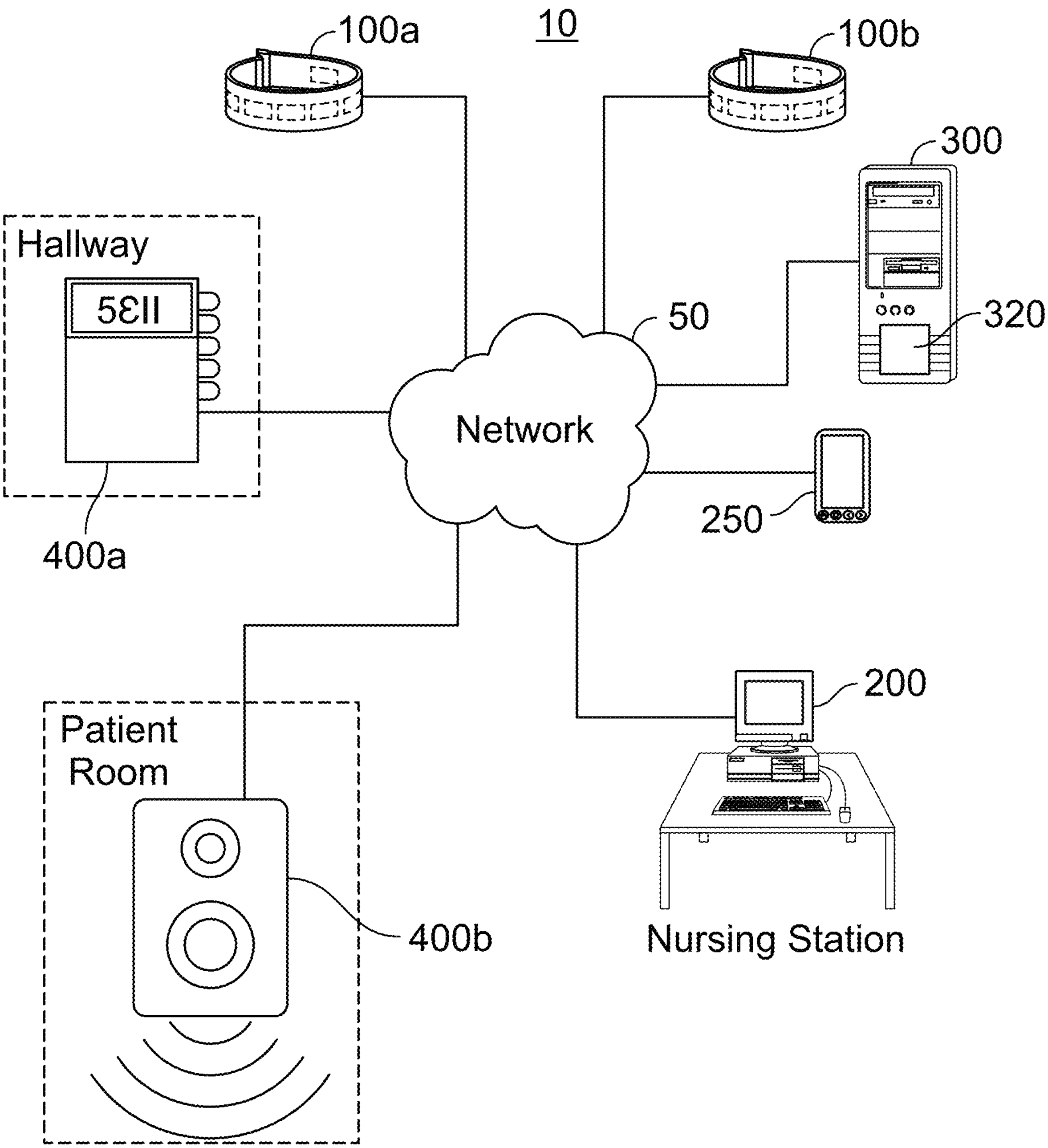
FIG. 4 is a schematic diagram showing a networked computing environment including the set of sensor bands of FIG. 1-3, in accordance with an exemplary embodiment of the present invention.

Alternatively, the IM 190 may be configured to initiate an intervention by sending the control signal to an alternative feedback device, such as an illuminated sign 400*a* (e.g., a room number display or room-associated lighting system or signage 400*a* in a hallway, adjacent each patient room) outside a patient's hospital room, or to a speaker 400*b* in the patient's hospital room, as shown in FIG. 4. This may involve transmitting the control signal via a network 50, as shown in FIG. 4. In certain embodiments, alerts may be color-coded (e.g., green means OK, yellow means that movement is detected indicating that the patient is preparing to exit the bed). In this manner, unassisted ambulation of the patient, and a resulting fall, can be avoided.

In certain embodiments, the IM 190 is configured to initiate an intervention by sending a control signal, e.g., via a network 50, to a remotely-located computing device 200, 250 (such as a smartphone, laptop/tablet/PC computer, etc.) that provides an alert to a caregiver or person who can intervene, in accordance with Intervention Data 124*e* stored in the Data Store 224 (such as contact/network information for sending the alert to the person), as shown in FIG. 4. For example, the IM 270 may send a control signal to cause display of a message or other indicator, or sounding of an alarm, at a nursing station, or a caregiver's computer, smartphone or other computing device, to alert the recipient of the prediction of imminent ambulation so that the person can take appropriate action. For example, the message may be displayed on a display device of the other device 200/250, e.g., as a banner notification, email, or text/SMS/MMS message, or otherwise.

In certain embodiments, some or all of the hardware, software and/or functionality may be implemented at a central computerized system 300 (having some or all of the components shown in reference to the sensor band 100*a*/100*b* in FIG. 3), such that at least some of the processing described with respect to the sensor band above may instead be performed at the central system 300. For example, in certain embodiments, the sensor band may not be configured to process the sensor data to make an ambulation prediction, but rather may transmit the sensor data to the central system 300, and the central system may process the sensor data to make the ambulation prediction. In such an embodiment, the central system may transmit the relevant control signal for implementing the intervention, e.g., via a network, as will be appreciated from FIG. 4.

In certain embodiments, the control signal may be transmitted to a caregiver's computing device 200/250 in the form of a wearable "status" band worn by the nurse/caregiver and integrated with the sensor bands 100*a*, 100*b*, central system 300, etc. Such a status band may have similar hardware and software as the sensor bands, but is further configured with the feedback device to provide alert information to the wearer of the status band.

In certain embodiments, monitoring information for at least one set of sensor bands may be provided to the nurse, e.g., via a dashboard display displayed on a computing device 200, 250 used by the nurse, etc. By way of example, the dashboard display may show a list of monitored patient rooms/patients, a band status (monitored/not monitored, moving/not moving, etc.), a battery level status of each band, etc.

In certain embodiments, the central system may include, or send information to, a tracking system 320 that is monitored by nurses/providers. The nurses/providers may provide input to the tracking system 320 (via a nurse validation interface displayed on a computing device 200, 250 used by the nurse, etc.) to identify whether the detected movement was in fact an attempt to leave the bed, or other motion in the nature of a "false alarm" (e.g., the patient rolling over in bed but not exiting the bed). This provides a feedback loop that is used by a machine learning model of the tracking system 320. In this manner, a learning model can be trained in detecting patients leaving beds, and distinguishing patients leaving beds from other movements detected by the sensors, to improve the accuracy of the system in detecting patients leaving beds and avoiding false alarms.

In certain embodiments, the dashboard display may show a list of monitored patient rooms/patients and an indication of whether information from the bands for each patient/room is being supplied to the tracking system. This allows the nurse to monitor the system, bands and patients collectively.

While there have been described herein the principles of the invention, it is to be understood by those skilled in the art that this description is made only by way of example and not as a limitation to the scope of the invention. Accordingly, it is intended by the appended claims, to cover all modifications of the invention which fall within the true spirit and scope of the invention.

What is claimed is:

1. A wearable device for predicting bodily falls, the device comprising:

a first sensor band dimensioned to be worn about a first limb of a living being; and a second sensor band dimensioned to be worn about a second limb of the living being;

each of said first and second sensor bands comprising:

at least one sensor operatively configured to collect sensor data associated with band movement; and a transceiver configured to transmit data from said at least one sensor via wireless data transmission; and at least one of said first and second sensor bands further comprising a data processor and a memory; and wherein said data processor is configured to process sensor data received from said first and second sensor bands by comparing at least one of acceleration, orientation, and position data received from each of said first and second sensor bands and to determine whether said sensor data indicates that ambulation of the living being is imminent.

2. The wearable device of claim 1, wherein each of said first and second sensor bands comprises a mounting body configured to mount the respective sensor band to a respective limb of the living being.

3. The wearable device of claim 1, wherein said at least one sensor is selected from a group consisting of an accelerometer, a gyroscope, and a global positioning system sensor.

4. The wearable device of claim 1, wherein the data processor is configured to process sensor data received from said first and second sensor bands by comparing at least one of acceleration, orientation, and position data received from each of said first and second sensor bands to determine whether the sensor data indicates that ambulation of the living being is imminent.

5. The wearable device of claim 1, wherein said data processor is configured to process said sensor data to analyze each sensor band's sensor data in relation to the other sensor band's sensor data.

6. The wearable device of claim 1, wherein said data processor is configured to process said sensor data to and to cause transmission of a control signal via the transceiver to deliver an intervention when the sensor data indicates that ambulation of the living being is imminent.

7. The wearable device of claim 1, further comprising a feedback device operable to provide at least one of a haptic, an audible and a visible alert signal to the living being.

8. The wearable device of claim 1, wherein said feedback device comprises at least one of a speaker, a vibratory motor, and a lamp.

9. A system for predicting bodily falls, the system comprising:

a first sensor band dimensioned to be worn about a wrist of a living being;

a second sensor band dimensioned to be worn about an ankle of the living being;

each of said first and second sensor bands comprising:

at least one sensor configured to collected data associated with band movement;

a transceiver operatively configured to transmit data from said at least one sensor via a communications network; and an external computing device comprising:

a data processor;

a communications device configured to receive sensor data via the communications network;

a memory; and instructions stored in said memory and executable by said data processor to cause said data processor analyze sensor data by comparing at least one of acceleration, orientation, and position data received from said first sensor band to similar data received from said second sensor band to determine whether the sensor data indicates that ambulation of the living being is imminent.

10. The system of claim 9, wherein said data processor is configured to process said sensor data to analyze each sensor band's sensor data in relation to the other sensor band's sensor data.

11. The system of claim 9, wherein said data processor is configured to process said sensor data and to cause transmission of a control signal via the communications device to a device monitored by a caregiver to prompt the caregiver to deliver an intervention when the sensor data indicates that ambulation of the living being is imminent.

12. The system of claim 11, wherein said device is a computing device operable to provide an alert prompt.

13. The system of claim 12, wherein said computing device comprises a display device operable to display at least one of an identification of a monitored sensor band, a monitored patient room, a monitored patient, and a battery level of the monitored sensor band.

14. The system of claim 11, wherein said device is a sign controllable to illuminate to display an alert prompt.

15. The system of claim 11, wherein said device is a status band wearable by a caregiver and controllable by the control signal to provide an alert prompt.

16. The system of claim 9, wherein said data processor is configured to process said sensor data and to cause transmission of a control signal via the communications device to a feedback device mounted in or near a room occupied by the living being, to drive the feedback device to alert the living being to avoid ambulation when the sensor data indicates that ambulation of the living being is imminent.

17. The system of claim 9, wherein at least one of said first and second sensor bands further comprises a feedback device operable to provide at least one of a haptic, an audible and a visible alert signal to the living being, and wherein said data processor is configured to process said sensor data and to cause transmission of a control signal via the communications device to said at least one of said first and second sensor bands to drive the feedback to device to alert the living being to avoid ambulation when the sensor data indicates that ambulation of the living being is imminent.

18. The system of claim 16, wherein said feedback device comprises at least one of a speaker, a vibratory motor, and a lamp.

19. The system of claim 16, wherein at least one of said first and second sensor bands further comprises a feedback device operable to provide at least one of a haptic, an audible and a visible alert signal to the living being.

20. The system of claim 9, wherein each of said first and second sensor bands comprises a mounting body configured to mount the respective sensor band to a respective limb of the living being.

21. The system of claim 9, wherein said at least one sensor is selected from a group consisting of an accelerometer, a gyroscope, and a global positioning system sensor.

22. A wearable device for predicting bodily falls, the device comprising:

a first sensor band dimensioned to be worn about a first limb of a living being; and a second sensor band dimensioned to be worn about a second limb of the living being;

each of said first and second sensor bands comprising:

at least one sensor operatively configured to collect sensor data associated with band movement, said at least one sensor is selected from a group consisting of an accelerometer, a gyroscope, and a global positioning system sensor; and a transceiver configured to transmit data from said at least one sensor via wireless data transmission; and a computing device comprising:

a data processor;

a memory; and instructions stored in said memory and executable by said data processor to compare at least one of acceleration, orientation, and position data of said received from each of said first and second sensor bands to determine whether the sensor data indicates that the living being is preparing or attempting to leave a bed or chair such that ambulation of the living being is imminent.

23. The wearable device of claim 22, wherein said each of said first and second sensor bands comprises a mounting body configured to mount the respective sensor band to a respective limb of the living being, and wherein said computing device is supported on at least one of said first and second sensor bands.

24. The wearable device of claim 22, wherein said computing device is an external computing device separate from said first and second sensor bands.

25. The wearable device of claim 22, wherein said data processor is configured to process said sensor data to analyze each sensor band's sensor data in relation to the other sensor band's sensor data.

26. The wearable device of claim 22, wherein said data processor is configured to process said sensor data to and to cause transmission of a control signal via a transceiver to deliver an intervention when the sensor data indicates that ambulation of the living being is imminent.

* * * * *